United States Patent
Sambanthamurthi et al.

(10) Patent No.: US 9,642,389 B2
(45) Date of Patent: May 9, 2017

(54) COMPOSITION COMPRISING OIL PALM PHENOLICS FOR USE IN PROVIDING NEUROPROTECTIVE EFFECTS AND COGNITIVE-ENHANCEMENT

(75) Inventors: Ravigadevi Sambanthamurthi, Selangor Darul Ehsan (MY); Soon-Sen Leow, Selangor (MY); Yew Ai Tan, Kuala Lumpur (MY); Kalyana Sundram P. Manickam, Selangor Darul Ehsan (MY); Mohd Basri Wahid, Selangor Darul Ehsan (MY)

(73) Assignee: MALAYSIAN PALM OIL BOARD, Selangor (MY)

( * ) Notice: Subject to any disclaimer, the term of this patent is extended or adjusted under 35 U.S.C. 154(b) by 644 days.

(21) Appl. No.: 13/145,101

(22) PCT Filed: Jan. 29, 2010

(86) PCT No.: PCT/MY2010/000019
§ 371 (c)(1),
(2), (4) Date: Oct. 26, 2011

(87) PCT Pub. No.: WO2010/087693
PCT Pub. Date: Aug. 5, 2010

(65) Prior Publication Data
US 2012/0040029 A1    Feb. 16, 2012

(30) Foreign Application Priority Data
Jan. 29, 2009  (MY) ............................... PI20090368

(51) Int. Cl.
*A61K 36/889* (2006.01)
*A23L 33/105* (2016.01)

(52) U.S. Cl.
CPC ......... *A23L 33/105* (2016.08); *A23V 2002/00* (2013.01)

(58) Field of Classification Search
CPC .............................. A61K 36/889; A61K 36/00
USPC ........................................................ 424/727
See application file for complete search history.

(56) References Cited

U.S. PATENT DOCUMENTS

| 2003/0031740 A1 | 2/2003 | Sambanthamurthi et al. |
| 2006/0024390 A1* | 2/2006 | Schauss et al. ............... 424/727 |

FOREIGN PATENT DOCUMENTS

| WO | WO-2008/127085 | 10/2008 |
| WO | WO-2008/127086 | 10/2008 |

OTHER PUBLICATIONS

Wattanapenpaiboon et al. "Phytonutrient deficiency: the place of palm fruit", Asia Pacific Journal Clinical Nutritional, 2003; 12(3), 363-368.*
Balasundram, et al., Antioxidant Properties of Palm Fruit Extracts, Asia Pac. J. Clin. Nutr., 4(4):319-324 (2005).
Neo, et al., Determination of Oil Palm Fruit Phenolic Compounds and Their Antioxidant Activities Using Spectrophotometric Methods, International Journal of Food Science & Technology, 43(10):1832-1837 (2008).
PCT International Search Report dated May 5, 2010 in related PCT Patent Appl Serial No. PCT/MY2010/000019.
Wattanapenpaiboon, et al., Phytonutrient Deficiency: The Place of palm fruit, Asia Pacific J. Clin. Nutr., 12(3):363-368 (2003).

* cited by examiner

*Primary Examiner* — Chris R Tate
*Assistant Examiner* — Deborah Davis
(74) *Attorney, Agent, or Firm* — Rahman LLC (57) ABSTRACT

The present invention relates to a composition comprising oil palm phenolics for use in providing neuroprotective effects and improving cognitive and motor functions abilities.

18 Claims, 6 Drawing Sheets

COMPOSITION COMPRISING OIL PALM PHENOLICS FOR USE IN PROVIDING NEUROPROTECTIVE EFFECTS AND COGNITIVE-ENHANCEMENT

FIELD OF INVENTION

The invention relates to a composition based on oil palm extract(s), and more particularly to a composition for use in providing neuroprotective effects and cognitive-enhancement properties.

BACKGROUND OF THE INVENTION

Harmful free radicals and reactive oxygen species have been implicated in aging and chronic diseases [1]. For instance, oxidative damage is particularly detrimental to the brain, where the neuronal cells are largely post-mitotic and those which are damaged cannot be replaced readily via mitosis [2]. During normal aging, the brain undergoes morphological and functional changes resulting in the observed neurobehavioural declines such as decrements in cognitive and motor performance, which leads to Alzheimer's disease (AD) and Parkinson's disease (PD) respectively. Prominent symptoms of Alzheimer's disease include memory loss and confusion, whilst common symptoms Parkinson's disease among others include trembling hands, arms, and face. It is understood that these symptoms are detrimental to the patient, particularly if appropriate medicinal relief is not provided.

Based on the above, various preventive measures which involve efforts to offer resistance against oxidative stress, including physical activity and dietary intervention, have been suggested to combat the advancement of chronic diseases as we age.

One of the effective resolutions which is evident based on studies conducted provides diets containing high amounts of phytochemicals, whereby activities in relation to protection against these free radical-induced diseases was observed, due to their high antioxidative activities [3]. Plant phenolics are especially important antioxidants because of their high redox potential, which allows them to act as reducing agents, hydrogen donors, singlet oxygen quenchers and metal chelators [3]. Antioxidants that accumulate in neuronal tissues are potential candidates for the prevention and treatment of neuronal disorders involving oxidative stress. Phenolic antioxidants may or may not cross the brain barrier, depending on their properties, such as charged state, lipophilicity and interactions with efflux transporters, with possible relative specificity of the compounds for different brain areas [4]. For example, proanthocyanidins from blueberries may be found in the striatum while ellagitannins from strawberries may involve the hippocampus [5]. Many studies have recently shown that plant phenolics are able to enhance cognitive performance, through their ability to reduce oxidative stress [2, 5-12].

In view of the above, it is clear that there is a need for an antioxidant composition preferably based on plant extract(s) which is able to provide significant neuroprotective effects and thus improve cognitive performance.

It is therefore a primary object of the present invention to fulfil this need and in particular to provide an effective method for prevention of neurodegenerative ailments in addition to improving cognitive performance due to oxidative stress.

On the basis that oil palm phenolics possess significant antioxidative activities [13, 14], it is hypothesized that they may have significant neuroprotective effects in vivo. Experiments were conducted on a balb/c mice on a normal diet fed with oil palm phenolics for six weeks for observation and thus verify the signs of improvement in brain functions.

SUMMARY OF INVENTION

The present invention is directed to a composition for use in prevention of neurodegenerative ailments and improving cognitive performance comprising phenolics compounds derived from an extract of oil palm.

In one embodiment of the present invention, the phenolic compounds are derived from an extract of oil palm by-products including vegetation liquor from the palm oil milling process, oil palm frond or oil palm fruit, and fresh fruit bunch.

There is provided a composition comprising phenolic compounds derived from an extract of oil palm used for providing neuroprotective effects and improving cognitive and motor functions.

BRIEF DESCRIPTION OF THE DRAWINGS

This invention will be described by way of non-limiting embodiments of the present invention, with reference to the accompanying drawings, in which.

DETAILED DESCRIPTION OF THE PRESENT INVENTION

In line with the above summary, the disclosed description and examples relates to a composition and method thereof for use in prevention of neurodegenerative diseases and improvement of cognitive performance. It shall be apparent to one skilled in the art that the exemplifications are provided to better elucidate the embodiments of the present invention and therefore should not be construed as limiting the scope of protection.

All methods described as exemplifications herein may be performed in any suitable order unless otherwise indicated herein.

For the experimental examples, inventors isolated botanical extracts comprising phenolic compounds, fruit acids, fruit sugars and glycerol from oil palm vegetation liquor from the palm oil milling process and the prepared formulations containing these extracts. It is understood that the extracts may be prepared by way of conventional methods.

All male inbred balb/c mice which were designated for the purpose of the present invention were purchased from the Institute of Medical Research, Kuala Lumpur, Malaysia, at around 5 weeks of age just after weaning. All animal procedures were approved by the Animal Care and Use Committee of the University of Malaya, Kuala Lumpur, Malaysia. The animals were randomly assigned into cages (5 animals/cage) and acclimatized for 1 week, during which a standard chow diet purchased from the University of Malaya, and distilled water were given.

It is noted that at the start of the experiment, the diet of the animals was changed to a custom-made standard normal diet (58.2% kcal/kcal carbohydrate, 27.2% kcal/kcal protein and 14.6% kcal/kcal fat, including cellulose, mineral mix, vitamin mix and DL-methonine). The control group (n=5) was supplemented with distilled water as drinks ad libitum while the treatment group (n=5) was supplemented with oil palm phenolics. The antioxidant content of the oil palm phenolics given was around 1500 ppm gallic acid equivalent. The oil palm phenolics were changed at least once a day as the oxidation of these compounds was rapid due to their high antioxidative activities. Mice were subjected to water maze and rotarod trials once a week throughout the feeding period. After 6 weeks of feeding, the mice were sacrificed via euthanasia with diethyl ether. Their brains were excised, blotted, snap-frozen in liquid nitrogen and stored at −80° C. until the total RNA extraction process for microarray analysis. The experiments conducted will be elucidated shortly herein.

Water Maze

Improved Cognitive Function and Memory Analysis

The water maze experiment is based upon the premise that animals have evolved an optimal strategy to explore their environment and escape from water with a minimum effort by swimming the shortest distance possible. The two major advantages of the water maze over other dry mazes such as the radial arm maze is that the animals do not need to be water or food deprived as they are quite motivated to escape from water, and the water maze task is also free from errors of omission or abortive choices as the animal will definitely make an attempt to find the platform on every trial.

Mice in both the control and treatment groups were tested in a water maze every week throughout the feeding period. The water maze (100 cm diameter and 60 cm height) was filled with water 1 cm above a transparent platform (11 cm diameter and 30 cm height), with a temperature of 26° C. The platform was placed at a permanent position in the north-east quadrant of the maze while each mouse was released at the same position for each trial in the south-west quadrant of the maze, with its head pointed towards the side of the water maze. Various external cues were available and visible to each mouse swimming in the water maze, such as the door, lights, several equipment, the computer and the experimenter. Each mouse was tracked by using a Panasonic WV-CP280/G colour CCTV camera, which was suspended 90° about 200 cm above the center of the water level and connected to an Euresys Picolo Diligent sn/219 frame grabber board installed in a desktop with Microsoft® Windows XP.

Each trial started 3 seconds after a mouse was in the arena (which was defined as the circular water border in the maze) and stopped at a maximum duration of 60 seconds (after which the mouse was guided to the platform and left to stay there for 10 seconds) or 10 seconds after the mouse found and stayed on the platform. The latency to the platform, the mean distance to the platform and the mean velocity of each mice were recorded by the Ethovision XT video tracking system and software (Noldus Information Technology, Wageningen, The Netherlands). Each mouse was tested four times during each time point with a rest period of about 5 minutes in between trials. Each mouse was towel dried after each trial before being returned to a holding cage. The first trial was excluded during data analysis as it served the purpose of acclimatizing the mouse to the maze after a week's gap from the last trial. The remaining three trials for each mouse were averaged and statistical analysis using a two-tailed Student's t-test was carried out on these average values in Microsoft Excel with a P<0.05 considered significant.

Results

Figures 1, 1C:
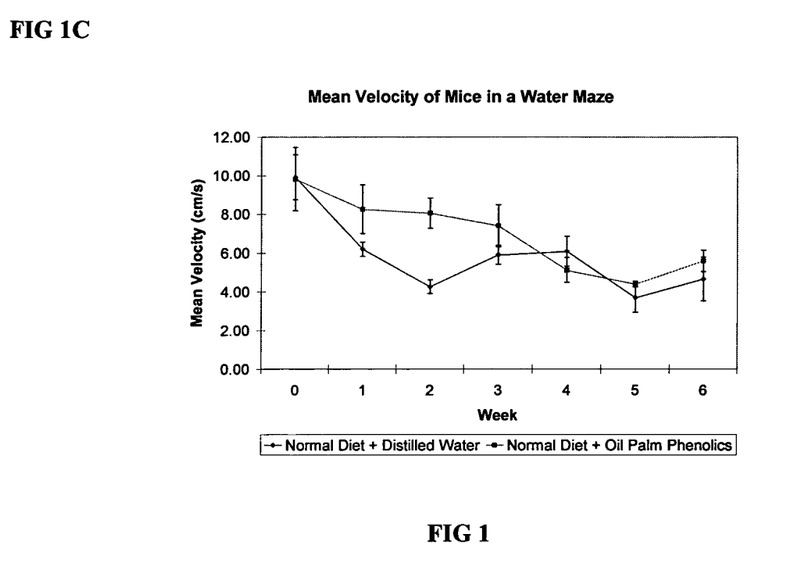
FIG. 1A to FIG. 1C plot the results obtained based on the water maze experiment for the purpose of the present invention.
Figure 1A:
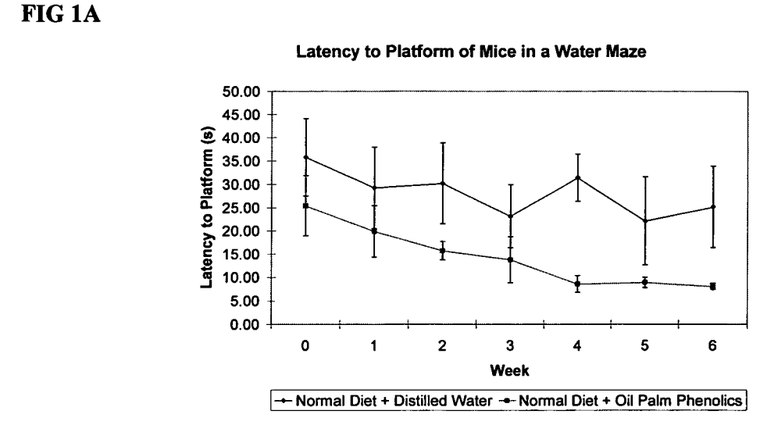
Figure 1B:
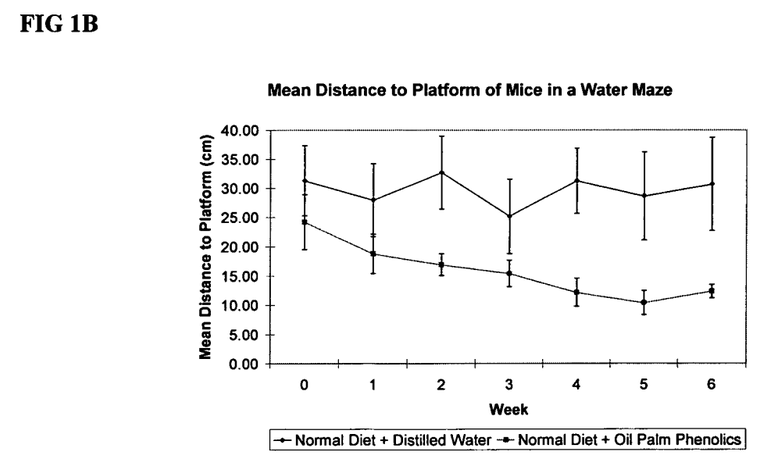

FIG. 1 provides the plotted results of the water maze trials, in which mice given oil palm phenolics showed a significant decrease in the latency to the platform (FIG. 1A) and mean distance to the platform (FIG. 1B), when compared to the controls. It is observed that these cognitive-enhancing effects are in line with those brought about by other phenolic antioxidants such as those from ginger [6], gingko [6, 15], apple [7], berry [2, 5, 8], green tea [9, 10], red wine [11] and pomegranate [12]. Although the mean velocity of mice in the treatment group was slightly increased at the beginning of the treatment (FIG. 1C), it can be seen that the change was not significant towards the end of the feeding period, thus indicating an improvement in memory instead of swimming speed in these mice towards the end of the treatment. This is in agreement with the effects of Zingicomb, a mixture of ginger and gingko extracts [6].

Rotarod

Improved Motor Function and Balance Analysis

In the second analysis mice in both groups were also tested on a five-laned IITC 755 Series 8 rotarod (IITC Life Science, Inc., Woodland Hills, Calif.) every week throughout the feeding period. The rotarod was started at 4 rpm and accelerated to 40 rpm over a period of 5 minutes in forward mode, with a rest period of about 3 minutes in between trials. Each mouse was tested four times during each time point, but the first trial was excluded during data analysis as it served the purpose of acclimatizing the mouse to the rotarod after a week's gap from the last trial. The remaining three trials for each mouse were averaged and statistical analysis using a two-tailed Student's t-test was carried out on these average values in Microsoft Excel, with a P<0.05 considered significant.

Results

Figure 2A:
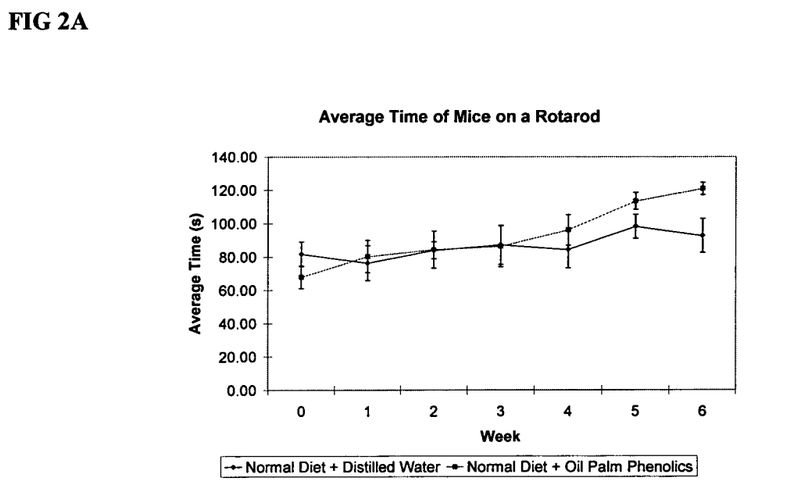
FIG. 2A to 2C plot the results obtained based on the rotarod experiment for the purpose of the present invention.
Figure 2B:
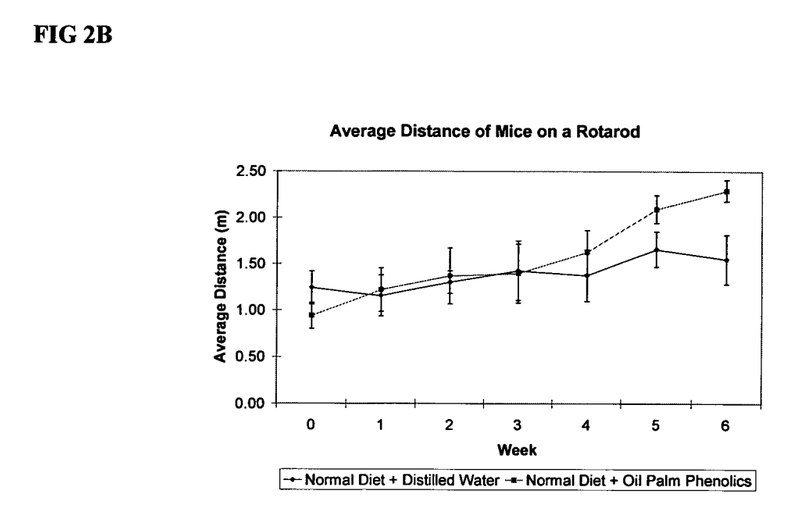
Figure 2C:
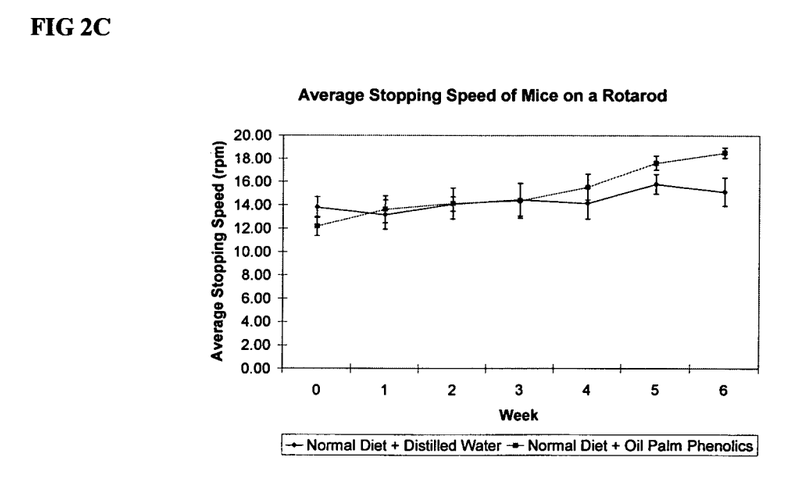

FIG. 2 provides the plotted results for this experiment in which mice supplemented with oil palm phenolics were found to have improved balance and motor coordination, as their average time (FIG. 2A), average distance travelled (FIG. 2B) and average stopping speed (FIG. 2C) before they fell from the rotating drums of the rotarod were higher when compared to the controls. These data are in line with several studies which showed that resveratrol [16] and several plant extracts such as those from Cistanches salsa [17], Polygala paniculata [18], Hypericum perforatum [19] and Withania somnifera [20], were able to improve the performance of mice on rotarods.

Microarray Analysis

Up-Regulation of Synaptogenesis and Neurotransmission Genes and Down-Regulation of Inflammatory Genes in the Brain For this experiment, microarray analysis is preferred, whereby it is one of the primary tools for dissecting molecular mechanisms in relation to antioxidants function and modulation of gene expression. Generally, microarrays are known for identification of important regulated genes or biomarkers, in addition to detection of combined effect of several genes belonging to a similar biological pathway [22]. Additionally, phytochemicals are also known to influence gene expression [23]. Microarray analysis thus becomes an important tool to identify modulations of multiple gene networks caused by antioxidant micronutrients [25]. Concordantly, in order to identify the possible molecular mechanisms involved in the neuroprotective properties of oil palm phenolics, microarray analysis was carried out on brains harvested from mice in the control and treatment groups. Further, this approach for analysis is preferred considering the fact that multi-component and multi-target botanical therapeutics administered through dietary interventions are highly valuable [21], for long-term prevention and treatment of complex diseases, despite the small effect on substantial number of genes of dietary interventions as compared to pharmaceutical interventions.

Total RNA isolation from mouse brains was first carried out using the RNeasy Mini Kit (Qiagen, Inc., Valencia, Calif.) and QIAshredder homogenizer (Qiagen, Inc., Valencia, Calif.) according to manufacturer's instructions. The total RNA samples obtained were subjected to NanoDrop 1000A Spectrophotometer for yield and purity assessment. Integrity of the total RNA samples was then assessed using the Agilent 2100 Bioanalyzer (Agilent Technologies, Palo Alto, Calif.) and Agilent RNA 6000 Nano Chip Assay Kit (Agilent Technologies, Palo Alto, Calif.). Four total RNA samples with the highest RNA Integrity Numbers and 28S/18S rRNA ratios within each condition (either control or treatment) were then selected for microarray studies.

Amplification of total RNA samples which were of high yield, purity and integrity was then carried out using the Illumina TotalPrep RNA Amplification Kit (Ambion, Inc., Austin, Tex.) according to manufacturer's instructions. The cRNA produced was then hybridized to the Illumina MouseRef-8 Expression BeadChip (Illumina, Inc., San Diego, Calif.), using the Direct Hybridization Kit (Illumina, Inc., San Diego, Calif.). Illumina MouseRef-8 Expression BeadChips contained 50-mer gene-specific probes for over 24000 genes which were designed based on the Mouse Exonic Evidence Based Oligonucleotide (MEEBO) set, the RIKEN FANTOM 2 database and the National Center for Biotechnology Information (NCBI) RefSeq (Release 5) transcript database. Microarray hybridization, washing and scanning were carried out according to the manufacturer's instructions.

Quality control of the hybridization, microarray data extraction and initial analysis were carried out using the Illumina BeadStudio software (Illumina, Inc., San Diego, Calif.). Outlier samples were removed via hierarchical clustering analysis provided by the Illumina BeadStudio software and also using the TIGR MeV software [26], via different distance metrics. A minimum of three replicates per condition (with outliers removed) was then considered for further analysis. Gene expression values were normalized using the rank invariant method and genes which had a Detection Level of more than 0.99 in either the control or treatment samples were considered significantly detected. To filter the data for genes which changed significantly in terms of statistics, the Illumina Custom error model was used and genes were considered significantly changed at a |Differential Score| of more than 13, which was equivalent to a P Value of less than 0.05 [27]. Using this filtering stringency, 113 genes were found to be up-regulated while 145 genes were down-regulated in brains of mice on a standard normal diet given oil palm phenolics when compared to the controls, as provided in FIG. 3.

The genes and their corresponding data were then exported into the Microsoft Excel software for further analysis. To calculate fold changes, an arbitrary value of 10 was given to expression values which were less than 10. Fold changes were then calculated by dividing means of Signal Y (treatment) with means of Signal X (control) if the genes were up-regulated and vice versa if the genes were down-regulated. Two-way (gene and sample) hierarchical clustering of the significant genes was then performed using the TIGR MeV software to ensure that the replicates of each condition were clustered to each other. The Euclidean distance metric and average linkage method were used to carry out the hierarchical clustering analysis.

Changes in biological pathways and gene ontologies were assessed via functional analysis, using the GenMAPP [28] and MAPPFinder [29] softwares. The MAPPFinder software ranks GenMAPPs (pathways) and gene ontologies based on the hypergeometric distribution. Readers are referred to [29] for further explanations of the terms used in the MAPPFinder software. GenMAPPs and gene ontologies which had Permuted P Values of less than 0.05, Numbers of Genes Changed of more than or equal to 2 and Z Scores of more than 2 were considered significant. Up- and down-regulated genes were analyzed separately in this functional enrichment analysis. It should be noted that the MAPPFinder software clusters multiple probes for a distinct gene into a single gene grouping in order to calculate the number of distinct genes which meet the user-defined criteria, not the probes.

The GenMAPPs and gene ontologies considered significantly up-regulated are shown in TABLE 1 below. Most of the significant functions up-regulated in brains of mice include those involved in neurotrophic activity. These include functions such as nervous system development, neurotransmitter transport, striated muscle contraction, synaptic transmission, synaptogenesis, calcium ion binding, calmodulin binding, potassium ion transport and transmembrane receptor protein tyrosine phosphatase activity.

TABLE 1

GenMAPPs and Gene Ontologies Significantly Up-Regulated by Oil Palm Phenolics in the Brain

GENMAPP

| No. | MAPP Name | Number Changed | Number Measured | Number on MAPP | Percent Changed | Percent Present | Z Score | Permuted P Value |
|---|---|---|---|---|---|---|---|---|
| 1 | Mm_Striated_muscle_contraction | 3 | 42 | 45 | 7.1429 | 93.3333 | 4.8690 | 0.0010 |
| 2 | Mm_IL-6_NetPath_18 | 5 | 96 | 97 | 5.2083 | 98.9691 | 5.1700 | 0.0030 |

TABLE 1-continued

GenMAPPs and Gene Ontologies Significantly Up-Regulated by Oil Palm Phenolics in the Brain

| 3 | Mm_Wnt_NetPath_8 | 4 | 106 | 109 | 3.7736 | 97.2477 | 3.6930 | 0.0070 |
| 4 | Mm_Delta-Notch_NetPath_3 | 3 | 78 | 80 | 3.8462 | 97.5000 | 3.2330 | 0.0230 |
| 5 | Mm_TGF-beta-Receptor_NetPath_7 | 4 | 141 | 148 | 2.8369 | 95.2703 | 2.9570 | 0.0270 |
| 6 | Mm_EGFR1_NetPath_4 | 4 | 166 | 171 | 2.4096 | 97.0760 | 2.5620 | 0.0290 |
| 7 | Mm_Insulin_Signaling | 4 | 152 | 159 | 2.6316 | 95.5975 | 2.7730 | 0.0320 |

GENE ONTOLOGY

| No. | GO Name | GO Type | Number Changed | Number Measured | Number in GO | Percent Changed | Percent Present | Z Score | Permuted P Value |
|---|---|---|---|---|---|---|---|---|---|
| 1 | exocytosis | P | 5 | 67 | 70 | 7.4627 | 95.7143 | 6.9960 | 0.0000 |
| 2 | synapse | C | 6 | 143 | 152 | 4.1958 | 94.0790 | 5.3380 | 0.0000 |
| 3 | antimicrobial humoral response (sensu Vertebrata) | P | 3 | 48 | 51 | 6.2500 | 94.1177 | 4.8660 | 0.0010 |
| 4 | transmembrane receptor protein tyrosine phosphatase activity | F | 2 | 13 | 14 | 15.3846 | 92.8571 | 6.6500 | 0.0020 |
| 5 | synaptic transmission | P | 7 | 232 | 254 | 3.0172 | 91.3386 | 4.5580 | 0.0020 |
| 6 | calcium ion binding | F | 12 | 742 | 812 | 1.6173 | 91.3793 | 3.4040 | 0.0030 |
| 7 | potassium channel activity | F | 4 | 119 | 139 | 3.3613 | 85.6115 | 3.7230 | 0.0040 |
| 8 | cell-cell signaling | P | 9 | 496 | 530 | 1.8145 | 93.5849 | 3.3180 | 0.0050 |
| 9 | cytoskeleton | C | 11 | 743 | 859 | 1.4805 | 86.4959 | 2.9280 | 0.0060 |
| 10 | nervous system development | P | 10 | 585 | 624 | 1.7094 | 93.7500 | 3.2900 | 0.0070 |
| 11 | potassium ion transport | P | 4 | 144 | 166 | 2.7778 | 86.7470 | 3.2190 | 0.0090 |
| 12 | synaptogenesis | P | 2 | 22 | 23 | 9.0909 | 95.6522 | 4.9590 | 0.0100 |
| 13 | metal ion binding | F | 29 | 2931 | 3379 | 0.9894 | 86.7416 | 2.6160 | 0.0100 |
| 14 | protein tyrosine phosphatase activity | F | 3 | 68 | 79 | 4.4118 | 86.0760 | 3.8950 | 0.0110 |
| 15 | membrane fraction | C | 9 | 588 | 630 | 1.5306 | 93.3333 | 2.7450 | 0.0110 |
| 16 | synaptosome | C | 2 | 31 | 33 | 6.4516 | 93.9394 | 4.0480 | 0.0130 |
| 17 | integral to plasma membrane | C | 13 | 966 | 1029 | 1.3458 | 93.8776 | 2.8240 | 0.0130 |
| 18 | potassium ion binding | F | 3 | 85 | 88 | 3.5294 | 96.5909 | 3.3370 | 0.0170 |
| 19 | cation channel activity | F | 5 | 234 | 265 | 2.1368 | 88.3019 | 2.8800 | 0.0180 |
| 20 | protein binding | F | 42 | 4724 | 5185 | 0.8891 | 91.1090 | 2.5600 | 0.0180 |
| 21 | plasma membrane | C | 18 | 1634 | 1760 | 1.1016 | 92.8409 | 2.4560 | 0.0180 |
| 22 | voltage-gated potassium channel activity | F | 3 | 91 | 105 | 3.2967 | 86.6667 | 3.1750 | 0.0210 |
| 23 | neurotransmitter transport | P | 2 | 41 | 42 | 4.8780 | 97.6191 | 3.3960 | 0.0260 |
| 24 | cation transport | P | 7 | 457 | 529 | 1.5317 | 86.3894 | 2.4120 | 0.0270 |
| 25 | diacylglycerol binding | F | 2 | 40 | 41 | 5.0000 | 97.5610 | 3.4500 | 0.0320 |
| 26 | calmodulin binding | F | 3 | 98 | 102 | 3.0612 | 96.0784 | 3.0030 | 0.0320 |
| 27 | intracellular signaling cascade | P | 13 | 1106 | 1204 | 1.1754 | 91.8605 | 2.3000 | 0.0350 |
| 28 | protein amino acid dephosphorylation | P | 3 | 122 | 136 | 2.4590 | 89.7059 | 2.5180 | 0.0440 |
| 29 | GTP binding | F | 5 | 301 | 335 | 1.6611 | 89.8508 | 2.2310 | 0.0490 |

On the other hand, genes involved in acute phase response, aldehyde metabolism, hormone-mediated signalling, lipid metabolism, oxidoreductase activity, prostaglandin synthesis regulation, tumour necrosis factor-alpha/nuclear factor-kappaB (TNF-α/NF-κB) signalling, focal adhesion and amino acid metabolism on the other hand, were down-regulated as shown in TABLE 2.

TABLE 2

GenMAPPs and Gene Ontologies Significantly Down-Regulated by Oil Palm Phenolics in the Brain

GENMAPP

| No. | MAPP Name | Number Changed | Number Measured | Number on MAPP | Percent Changed | Percent Present | Z Score | Permuted P Value |
|---|---|---|---|---|---|---|---|---|
| 1 | Mm_Prostaglandin_synthesis_regulation | 3 | 31 | 31 | 9.6774 | 100.0000 | 4.1950 | 0.0080 |
| 2 | Mm_TNF-alpha-NF-kB_NetPath_9 | 6 | 167 | 176 | 3.5928 | 94.8864 | 2.7330 | 0.0100 |
| 3 | Mm_Alanine_and_aspartate_metabolism | 2 | 13 | 42 | 15.3846 | 30.9524 | 4.5510 | 0.0110 |
| 4 | Mm_Integrin-mediated_cell_adhesion_KEGG | 4 | 90 | 98 | 4.4444 | 91.8367 | 2.7170 | 0.0190 |
| 5 | Mm_T-Cell-Receptor_NetPath_11 | 5 | 124 | 126 | 4.0323 | 98.4127 | 2.7860 | 0.0260 |
| 6 | Mm_Focal_adhesion_KEGG | 6 | 181 | 190 | 3.3149 | 95.2632 | 2.5090 | 0.0260 |
| 7 | Mm_Hedgehog_Netpath_10 | 2 | 21 | 22 | 9.5238 | 95.4545 | 3.3850 | 0.0330 |
| 8 | Mm_Valine_leucine_and_isoleucine_degradation | 2 | 27 | 44 | 7.4074 | 61.3636 | 2.8560 | 0.0390 |

TABLE 2-continued

GenMAPPs and Gene Ontologies Significantly Down-Regulated by Oil Palm Phenolics in the Brain

GENE ONTOLOGY

| No. | GO Name | GO Type | Number Changed | Number Measured | Number in GO | Percent Changed | Percent Present | Z Score | Permuted P Value |
|---|---|---|---|---|---|---|---|---|---|
| 1 | aldehyde metabolism | P | 3 | 9 | 10 | 33.3333 | 90.0000 | 10.3410 | 0.0000 |
| 2 | oxidoreductase activity | F | 17 | 663 | 775 | 2.5641 | 85.5484 | 4.6740 | 0.0000 |
| 3 | aldehyde reductase activity | F | 2 | 5 | 5 | 40.0000 | 100.0000 | 9.2900 | 0.0010 |
| 4 | membrane fraction | C | 13 | 588 | 630 | 2.2109 | 93.3333 | 3.4610 | 0.0010 |
| 5 | cytoplasm | C | 48 | 3488 | 3969 | 1.3761 | 87.8811 | 3.4600 | 0.0010 |
| 6 | endoplasmic reticulum | C | 11 | 529 | 561 | 2.0794 | 94.2959 | 2.9490 | 0.0050 |
| 7 | Rho GTPase activator activity | F | 2 | 17 | 17 | 11.7647 | 100.0000 | 4.7640 | 0.0060 |
| 8 | electron transporter activity | F | 6 | 175 | 195 | 3.4286 | 89.7436 | 3.5830 | 0.0060 |
| 9 | actin filament organization | P | 3 | 45 | 47 | 6.6667 | 95.7447 | 4.1200 | 0.0070 |
| 10 | hormone-mediated signaling | P | 2 | 10 | 11 | 20.0000 | 90.9091 | 6.4200 | 0.0080 |
| 11 | lipid metabolism | P | 11 | 581 | 616 | 1.8933 | 94.3182 | 2.6100 | 0.0110 |
| 12 | protein kinase binding | F | 3 | 53 | 62 | 5.6604 | 85.4839 | 3.6920 | 0.0130 |
| 13 | ruffle | C | 2 | 23 | 26 | 8.6957 | 88.4615 | 3.9770 | 0.0140 |
| 14 | focal adhesion | C | 2 | 24 | 26 | 8.3333 | 92.3077 | 3.8740 | 0.0200 |
| 15 | GTPase activator activity | F | 4 | 119 | 132 | 3.3613 | 90.1515 | 2.8700 | 0.0210 |
| 16 | acute-phase response | P | 2 | 23 | 26 | 8.6957 | 88.4615 | 3.9770 | 0.0240 |
| 17 | actin filament | C | 2 | 25 | 27 | 8.0000 | 92.5926 | 3.7770 | 0.0250 |
| 18 | catalytic activity | F | 54 | 4696 | 5420 | 1.1499 | 86.6421 | 2.2540 | 0.0260 |
| 19 | cytosol | C | 7 | 345 | 383 | 2.0290 | 90.0783 | 2.2660 | 0.0270 |
| 20 | NADH dehydrogenase activity | F | 2 | 31 | 43 | 6.4516 | 72.0930 | 3.2900 | 0.0290 |
| 21 | isomerase activity | F | 4 | 136 | 153 | 2.9412 | 88.8889 | 2.5480 | 0.0310 |
| 22 | NAD binding | F | 2 | 30 | 53 | 6.6667 | 56.6038 | 3.3620 | 0.0360 |
| 23 | microsome | C | 4 | 138 | 148 | 2.8986 | 93.2432 | 2.5130 | 0.0380 |
| 24 | neurotransmitter transport | P | 2 | 41 | 42 | 4.8780 | 97.6191 | 2.7130 | 0.0470 |
| 25 | lyase activity | F | 4 | 149 | 165 | 2.6846 | 90.3030 | 2.3330 | 0.0470 |
| 26 | intracellular signaling cascade | P | 16 | 1106 | 1204 | 1.4467 | 91.8605 | 2.0290 | 0.0480 |

Changes in regulatory networks were also analyzed through the use of Ingenuity Pathways Analysis software (Ingenuity® Systems, Redwood City, Calif.) [30]. A data set containing differentially expressed genes and their corresponding fold changes was uploaded into the application. Analysis of up- and down-regulated genes was carried out separately. Each gene identifier was mapped to its corresponding gene object in the Ingenuity Pathways Knowledge Base. These genes were overlaid onto a global molecular network developed from information contained in the Ingenuity Pathways Knowledge Base. Networks of these focus genes were then algorithmically generated based on their connectivity.

A network can be used for providing a graphical representation of the molecular relationships between genes/gene products. Genes or gene products are represented as nodes, and the biological relationship between two nodes is represented as an edge (line). The intensity of the node color indicates the degree of up- (red) or down- (green) regulation. Nodes are displayed using various shapes that represent the functional class of the gene product. Edges are displayed with various labels that describe the nature of the relationship between the nodes. Gene descriptions which were not referenced emanated directly from the Ingenuity Pathways Analysis software.

Figure 3:
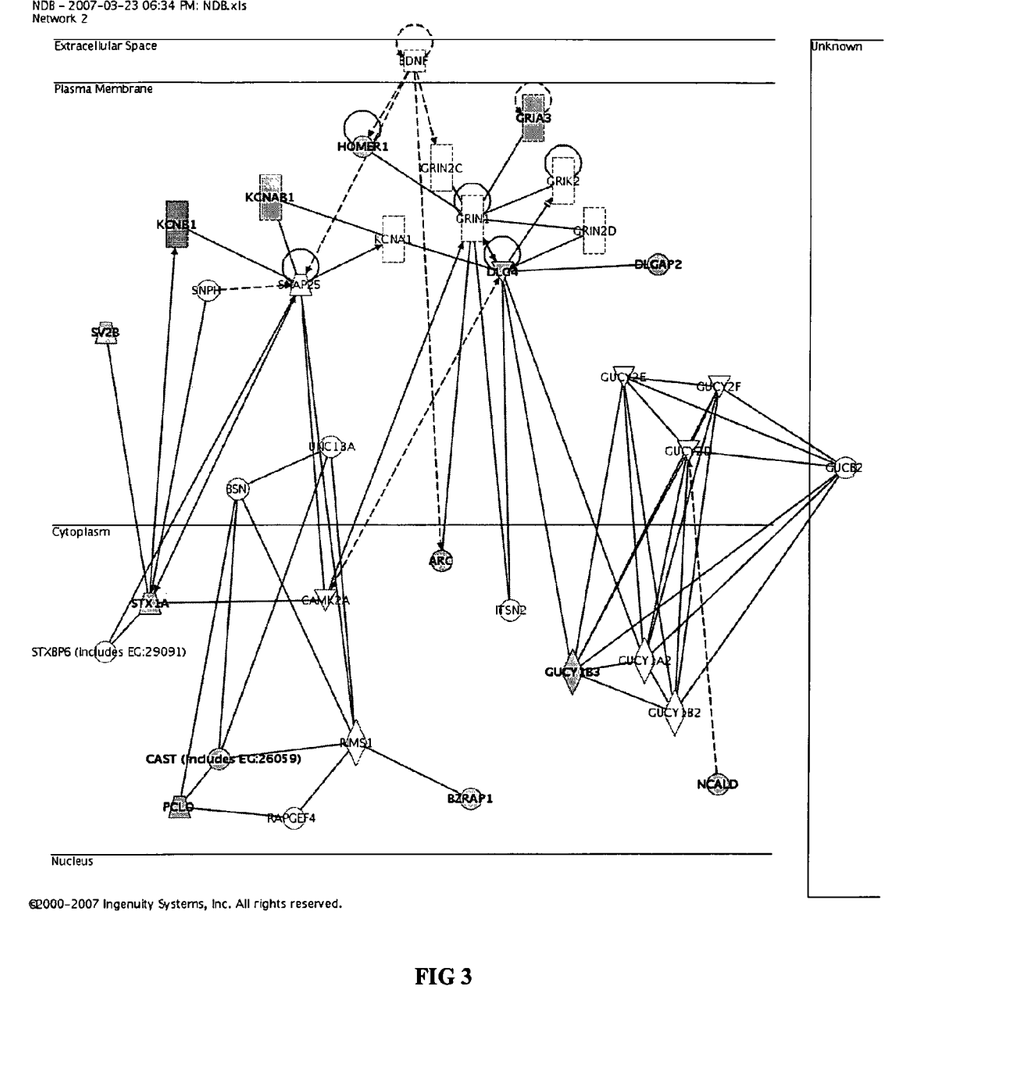
FIG. 3 illustrates the gene up-regulation in brain neurotrophic network in accordance with an embodiment of the present invention.

An up-regulated network obtained by this analysis is shown in FIG. 3. It is observed that Arc, Cast, Gria3, Kcnb1, Kcnab1, Homer1, Dlgap2, Dlgh4, Sv2b, Stx1a, Gucy1b3, Ncald, Bzrap1 and Pclo are under the regulation of the brain-derived neurotrophic factor (Bdnf), and this represents a network by which oil palm phenolics up-regulated genes involved in neuronal network maintenance and signalling.

Figure 4:
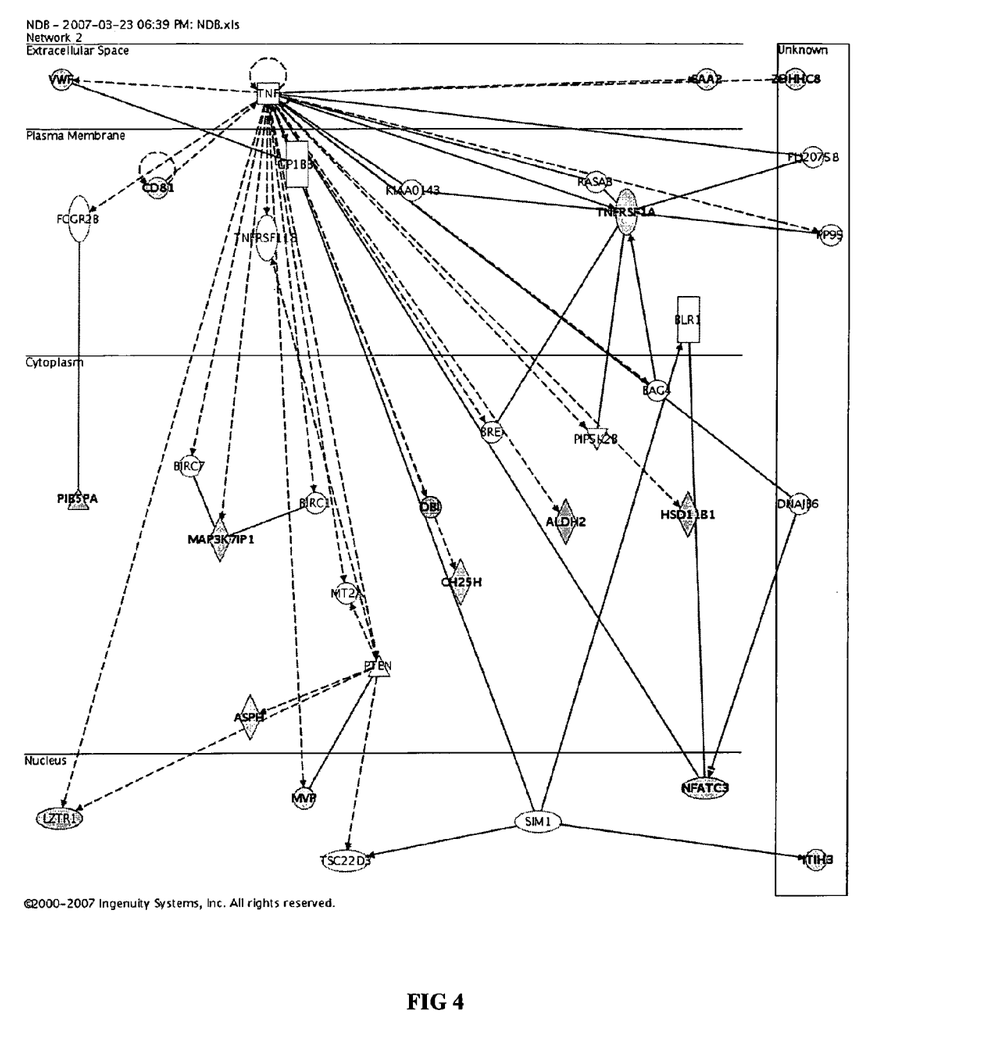
FIG. 4 illustrates the gene down-regulation in brain inflammatory network in accordance with an embodiment of the present invention.

FIG. 4 provides a down-regulated network, whereby genes under the regulation of Tnf such as Vwf, Tnfrsf1a and Saa were down-regulated, indicating a reduction in inflammation in brains of mice given oil palm phenolics.

Overall, genes in several pathways were found to be regulated in brains of mice supplemented with oil palm phenolics. For example, genes which are involved in calcium ion binding, calmodulin binding, potassium ion transport and transmembrane receptor protein tyrosine phosphatase activity were up-regulated. It is interesting to note that these genes are implicated to have neuroprotective roles, as similar genes were found to be up-regulated by extracts of Gingko biloba leaves [31], which are already marketed as supplements to combat Alzheimer's disease, depression, short-term memory loss as well as lack of attention and vigilance. Tyrosine phosphatase is associated with the formation or breakdown of intracellular neurofibrillary tangles, a hallmark lesion of Alzheimer's disease, while ionotropic glutamate receptor plays an integral role in synaptogenesis and the formation of neuronal circuitry [31]. Both of these types of genes (Ptprn, Ptprt and Gria3) were found to be up-regulated by oil palm phenolics.

Incidentally, genes involved in nervous system development, neurotransmitter transport, striated muscle contraction, synaptic transmission and synaptogenesis were also up-regulated, and these thereby support the observation that oil palm phenolics enhanced memory and cognitive function. Interestingly, many of these genes were under the regulation of Bdnf as suitably seen in FIG. 3, which influences the differentiation and survival of neurons and the maintenance of their arborizations. Bdnf is also involved in both short- and long-term plasticity of glutamatergic synapses as well as enhances synaptic maturation, increases synaptic density in the hippocampus and induces local dendritically targeted protein synthesis [32]. Although the Bdnf gene was not found to be significantly up-regulated in this study, the up-regulation of the genes directly under its regulation suggests that this gene may play a probable role as well, possibly at the protein level.

Transcription factors involved in protein synthesis such as Fos, Egr1 and Egr4 were also up-regulated (1.95-fold, 1.68-fold and 1.75-fold respectively). Incidentally, the rate of protein synthesis in brains of ovariectomized female rats were also found to be up-regulated by quercetin [33], an antioxidant found in apples, and this suggests that oil palm phenolics may increase the synthesis of proteins required for brain functions. The Fos gene for example, is a marker of neuronal activity and plasticity. The age-related decline of Fos in the hippocampi of aged rats was also found to be attenuated by the ginsenoside Rg1 from *Panax ginseng* [34].

The neuro-plasticity associated Arc gene which is a direct transcriptional target of Egr transcription factors, was also up-regulated by oil palm phenolics. Similar to the Egrs, the Arc gene is rapidly induced by synaptic activity, and its expression depends upon excitatory synaptic NMDA receptor activation and intracellular MAPK signalling, and it has a critical role in maintaining long-term potentiation and long-term memory [35]. Dlgh4 or Psd-95, is a post-synaptic marker which was significantly decreased by beta-amyloids but induced by withanosides from Ashwagandha (root of *Withania somnifera*), which is a herbal drug in ayurvedic medicine commonly used as a tonic and nootropic agent [36].

On the other hand, genes involved in acute phase response, aldehyde metabolism, hormone-mediated signalling, lipid metabolism, oxidoreductase activity, prostaglandin synthesis regulation and tumour necrosis factor-alpha/nuclear factor-kappaB (TNF-α/NF-κB) signalling, were down-regulated in brains of mice supplemented with oil palm phenolics. For example, the gene encoding secreted phosphoprotein 1 or osteopontin (Spp1), the gene encoding serum amyloid A 3 (Saa3) and the gene encoding apolipoprotein D (Apod) were down-regulated.

Osteopontin is a pro-inflammatory protein reported to be up-regulated in several types of cancer and multiple sclerosis [37]. The levels of serum amyloid A proteins which are members of the acute phase protein family, are increased in response to various injuries and have been implicated in the pathogenesis of chronic inflammatory diseases [38]. For example, the serum amyloid A 2 isoform is involved in amyloid formation in brain aging [39]. On the other hand, apolipoprotein D is associated with excitoxic stress resulting in brain aging [39, 40] and Parkinson's disease [41]. Other genes involved in inflammation such as Vwf and Tnfrsf1*a* were also down-regulated as provided in FIG. 4.

Genes involved in focal adhesion were also down-regulated in brains of mice given oil palm phenolics. Focal adhesion is a mechanism embodying the actin and cytoskeleton cell connections of a cell to the extracellular matrix. Actb, a normal housekeeping gene used for real-time polymerase chain reaction (PCR) studies and involved in focal adhesion, was found to be down-regulated. Actin is a cytoskeletal protein which is found in elevated amounts in Alzheimer's disease and in reactive glia. Its expression in the brain was found to be down-regulated by grape seed extract, which is enriched with proanthocyanidins [42]. Bcar1, a gene implicated in induction of cell migration and conferring anti-estrogen resistance on breast cancer cells when overexpressed [43], was down-regulated as well.

In addition, genes involved in alanine, aspartate, valine, leucine and isoleucine metabolism were down-regulated. The prevention of the oxidation of some amino acids by *Gingko biloba* had been implied in preventing the formation of amyloid β fibrils in Alzheimer's disease [44]. Other functions down-regulated include electron transporter activity, GTPase activator activity and intracellular signalling cascade. Dnajc4 which encodes a chaperone protein, was down-regulated. The up-regulation of a related gene expressing the DnaJ homologue 1 (Hsp40), was also found to be attenuated 100% by caloric restriction [39]. In addition, two homeobox genes (Hoxa5 and Hoxb5) have been turned off as their expression in the brain could not be detected after the supplementation of oil palm phenolics. Hoxb5 is up-regulated in incipient Alzheimer's disease [45].

The up-regulation of genes involved in brain development and activity as well as down-regulation of genes involved in inflammation in brains of mice thus further supports that oil palm phenolics have neuroprotective and anti-inflammatory effects. This is in line with the observations made when blueberry antioxidants were supplemented to F344 rats, in which the improvement in cognitive performance was related to an increase in neuronal signalling and neurogenesis [2]. In addition, these microarray results are also in correlation with the results of epicatechin supplementation to C57BL/6 mice, in which genes involved in learning were up-regulated while those involved in inflammation were down-regulated [10].

Real-Time qRT-PCR Analysis

Confirmation of Microarray Analysis

Two-step real-time qRT-PCR studies were carried out on two selected target genes, using TaqMan Gene Expression Assays (Applied Biosystems, Foster City, Calif.). The same aliquots of total RNA samples used in the microarray experiments were utilized for this analysis. Primer and probe sets for the selected genes were obtained from the ABI Inventoried Assays-On-Demand (Applied Biosystems, Foster City, Calif.). Reverse transcription to generate first-strand cDNA from total RNA was carried out using the High-Capacity cDNA Reverse Transcription Kit (Applied Biosystems, Foster City, Calif.). Real time PCR was then carried out on the first-strand cDNA generated using a 25 µL reaction volume in an ABI 7000 Real-Time PCR System (Applied Biosystems, Foster City, Calif.) according to manufacturer's instructions. Reactions for each biological replicate and non-template controls (NTCs) were carried out in duplicates.

Quality control of the replicates used, real-time qRT-PCR data extraction and initial analysis were carried out using the 7000 Sequence Detection System software (Applied Biosystems, Foster City, Calif.). A manual threshold of 0.6000 and an auto baseline were applied in order to obtain the threshold cycle (Ct) for each measurement taken. The threshold was chosen as it intersected the exponential phase of the amplification plots [46]. The criteria for quality control of the data obtained include $\Delta$Ct of less than 0.5 between technical replicates and $\Delta$Ct of more than 5.0 between samples and NTCs [47].

Relative quantification of the target genes of interest was carried out using the qBase 1.3.5 software [48], which takes into account the calculations of amplification efficiencies and multiple housekeeping genes. Expression levels of target genes were normalized to the geometric mean of three housekeeping genes, Sfrs9, Guk1 and Hnrpab. Stability of these housekeeping genes was assessed using the geNorm 3.5 software [49]. A statistical model for group-wise comparison, the Pair Wise Fixed Reallocation Randomization Test, embedded in the REST-384 2.0 software [50] was used for statistical analysis of the data obtained.

Results

Figure 5:
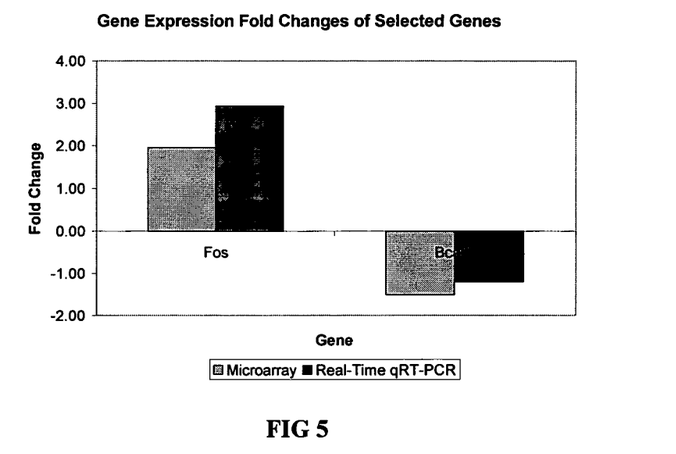
FIG. 5 provides a bar graph showing the gene expression fold two changes of two target genes as determined by microarray and real time qRT-PCR experiments for the purpose of the present invention.

The fold changes obtained from the real-time qRT-PCR technique were accepted as comparable to those obtained from the microarray technique as seen and plotted in FIG. 5 thus evidencing that the microarray data analysis carried out was reliable.

Dosage and Formulation

Generally, the composition comprising oil palm phenolics may be prepared in various suitable forms for direct or oral administration in a patient in need thereof, efficacious for providing neuroprotective effects, prevention of neurodegerative diseases and diseases related thereto and providing improvement of cognitive and motor functions.

The composition comprising oil palm phenolics of the present invention may be prepared for use in a pharmaceutically effective or nutraceutically effective amount, solely on its own or in combination with other agents or compounds deemed appropriate by a person skilled in the art.

It is noted that the term 'pharmaceutically effective' and 'nutraceutically effective' amount includes a quantification that is acceptable for providing neuroprotective effects, prevention of neurodegerative diseases and diseases related thereto and providing improvement of cognitive and motor functions properties.

In one embodiment the composition comprising oil palm phenolics may be administered in form of doses, within a predetermined period of time, whereby it may be administered for example but not limiting to daily, weekly or monthly.

In another embodiment the composition comprising oil palm phenolics may be provided in conventional treatment forms, pharmaceutical formulations or as nutritional supplement.

In one embodiment the composition of the present invention may be provided in a nutraceutical form.

It is understood by a person skilled in the art that the methods for experiments and studies are described as exemplifications herein and thus the results are not intended, however, to limit or restrict the scope of the invention in any way and should not be construed as providing conditions, parameters, agents or starting materials which must be utilized exclusively in order to practice the present invention. It is therefore understood that the invention may be practiced, within the scope of the appended claims, with equivalent methods for the experiments than as specifically described and stated in claims.

The invention claimed is:

1. A method for up-regulating at least one gene involved in neuroprotection in the brain of a subject in need thereof, the method comprising:
   administering to said subject a composition comprising an effective amount of an extract from oil palm vegetation liquor, wherein said extract contains a mixture of phenolic compounds, fruit adds, fruit sugars and glycerol, wherein said extract contains an antioxidant content of about 1500 ppm gallic add equivalent;
   wherein the amount of the composition administered is sufficient to up-regulate at least one gene involved in neuroprotection, wherein the gene is selected from the group consisting of Arc, Cast, Gria3, Kcnb1, Kcnab1, Homer1, Dlgap2, Dlgh4, Sv2b, Stx1a, Gucylb3, Ncald, Bzrap1, Pelo, Ptprn, Ptprt, Fas, Egr 1, and Egr4; and
   wherein said composition is administered in the form of doses on a daily, weekly or monthly basis for a predetermined period of time, thereby providing neuroprotection in the brain of said subject.

2. The method of claim 1, wherein the subject has at least one neurodegenerative disease or a disease related thereto.

3. The method of claim 1, wherein the composition improves cognitive and motor functions in the subject.

4. The method of claim 1, wherein the composition is administered in a dose dependent manner.

5. The method of claim 1, wherein the composition is administered in a liquid dosage form.

6. The method of claim 1, wherein the composition is administered in a pharmaceutically effective form.

7. The method of claim 1, wherein the composition is administered in a nutraceutical form.

8. The method of claim 1, wherein the composition is administered in a nutritional supplementary form.

9. The method of claim 1, wherein the composition is administered in a suppository form.

10. The method of claim 1, wherein the composition is administered in a form suitable for oral administration.

11. The method of claim 1, wherein the composition is administered in a form suitable for intravenous administration.

12. A method of reducing inflammation in the brain of a patient having a neurodegenerative disease, the method comprising:
   administering to said patient a composition comprising an effective amount of an extract from oil palm vegetation liquor, wherein said extract contains a mixture of phenolic, compounds, fruit adds, fruit sugars and glycerol, wherein said extract contains an antioxidant content of about 1500 ppm gallic add equivalent;
   wherein at least one gene involved in acute phase response, aldehyde metabolism, hormone-mediated signaling, lipid metabolism, oxidoreductase activity, prostaglandin synthesis regulation, tumor necrosis factor-alpha/nuclear factor-kappaB (TNF-alpha/NF-kappaB) signaling, focal adhesion, and/or amino add metabolism is down-regulated; and
   wherein said composition is administered in the form of doses on a daily, weekly or monthly basis for a predetermined period of time, thereby reducing inflammation in the brain of the patient.

13. The method of claim 12, wherein the composition improves cognitive and motor functions in the patient.

14. The method of claim 12, wherein the composition is administered in a dose dependent manner.

15. The method of claim 12, wherein the composition is administered in a liquid dosage form.

16. The method of claim 12, wherein the composition is administered in a pharmaceutically effective form.

17. The method of claim 12, wherein the composition is administered in a nutraceutical form.

18. A method for up-regulating tyrosine phosphatase and/or ionotropic glutamate receptor genes, and/or down-regulating at least one gene from the group consisting actin, Hoxa5, and Hoxb5 in the brain of a subject suffering from Alzheimer's Disease, the method comprising:
   administering to said subject a composition comprising an effective amount of an extract from oil palm vegetation liquor, wherein said extract contains a mixture of phenolic compounds, fruit acids, fruit sugars and glycerol, wherein said extract contains an antioxidant content of about 1500 ppm gallic acid equivalent; and
   wherein said composition is administered in the form of doses on a daily, weekly or monthly basis for a predetermined period of time, thereby up-regulating tyrosine phosphatase and/or ionotropic glutamate receptor genes, and/or down-regulating at least one gene from the group consisting actin, Hoxa5, and Hoxb5 in the brain of said subject.

\* \* \* \* \*